US010294263B2

(12) United States Patent
Miller et al.

(10) Patent No.: US 10,294,263 B2
(45) Date of Patent: May 21, 2019

(54) TRANSITION METAL MOLYBDOTUNGSTEN OXY-HYDROXIDE

(71) Applicant: UOP LLC, Des Plaines, IL (US)

(72) Inventors: Stuart Miller, Arlington Heights, IL (US); Susan C. Koster, Carpentersville, IL (US)

(73) Assignee: UOP LLC, Des Plaines, IL (US)

( * ) Notice: Subject to any disclaimer, the term of this patent is extended or adjusted under 35 U.S.C. 154(b) by 0 days.

(21) Appl. No.: 15/986,749

(22) Filed: May 22, 2018

(65) Prior Publication Data

US 2018/0265539 A1    Sep. 20, 2018

Related U.S. Application Data

(63) Continuation of application No. 15/377,714, filed on Dec. 13, 2016, now Pat. No. 10,005,812.

(Continued)

(51) Int. Cl.
B01J 21/10        (2006.01)
B01J 23/06        (2006.01)
(Continued)

(52) U.S. Cl.
CPC .......... *C07H 23/00* (2013.01); *B01J 23/8885* (2013.01); *B01J 35/002* (2013.01);
(Continued)

(58) Field of Classification Search
CPC ........ C10G 45/05; C10G 45/50; C10G 45/60; C10G 47/12; C10G 49/04; B01J 21/10; B01J 23/002; B01J 23/06; B01J 23/28; B01J 23/30; B01J 23/34; B01J 23/70; B01J 23/72; B01J 23/745; B01J 23/75; B01J 23/755; B01J 23/80; B01J 23/88;
(Continued)

(56) References Cited

U.S. PATENT DOCUMENTS 4,904,634 A *  2/1990  Wieserman ......... B01J 20/3248
                                                    502/401
2008/0280754 A1* 11/2008 Toledo Antonio ...... B01J 23/85
                                                    502/177
(Continued)

FOREIGN PATENT DOCUMENTS

CA    2719157 A1 * 10/2009 ............ B01J 23/002

OTHER PUBLICATIONS

"Remarkable improvement of the turn-on characteristics of a Fe2O3 photoanode for photoelectrochemical water splitting with coating a FeCoW oxy-hydroxy gel," Jingran Xiao et al. Applied Catalysis B: Environmental 212 (2017), pp. 89-96. (Year: 2017).*

(Continued)

*Primary Examiner* — Patricia L. Hailey

(57) ABSTRACT

A hydroprocessing catalyst has been developed. The catalyst is formed from a unique transition metal molybdotungsten oxy-hydroxide material. The hydroprocessing using the transition metal molybdotungsten oxy-hydroxide material-based catalyst may include hydrodenitrification, hydrodesulfurization, hydrodemetallation, hydrodesilication, hydrodearomatization, hydroisomerization, hydrotreating, hydrofining, and hydrocracking.

12 Claims, 1 Drawing Sheet

Related U.S. Application Data

(60) Provisional application No. 62/267,877, filed on Dec. 15, 2015.

(51) Int. Cl.

| | |
|---|---|
| *B01J 23/28* | (2006.01) |
| *B01J 23/30* | (2006.01) |
| *B01J 23/34* | (2006.01) |
| *B01J 23/70* | (2006.01) |
| *B01J 23/72* | (2006.01) |
| *C07H 23/00* | (2006.01) |
| *B01J 37/03* | (2006.01) |
| *B01J 23/888* | (2006.01) |
| *B01J 35/00* | (2006.01) |
| *B01J 37/00* | (2006.01) |
| *C10G 45/08* | (2006.01) |
| *C10G 45/50* | (2006.01) |
| *C10G 45/60* | (2006.01) |
| *C10G 47/12* | (2006.01) |
| *C10G 49/04* | (2006.01) |

(52) U.S. Cl.
CPC .......... *B01J 37/009* (2013.01); *B01J 37/0009* (2013.01); *B01J 37/031* (2013.01); *C10G 45/08* (2013.01); *C10G 45/50* (2013.01); *C10G 45/60* (2013.01); *C10G 47/12* (2013.01); *C10G 49/04* (2013.01)

(58) Field of Classification Search
CPC ...... B01J 23/881; B01J 23/882; B01J 23/883; B01J 23/885; B01J 23/888; B01J 23/8892
USPC ............... 208/108, 113, 209, 251 H, 254 H; 585/250, 477, 664; 502/171
See application file for complete search history.

(56) References Cited

U.S. PATENT DOCUMENTS

| | | | |
|---|---|---|---|
| 2015/0292095 A1* | 10/2015 | Haber | C25B 11/0452 502/304 |
| 2017/0165656 A1* | 6/2017 | Miller | B01J 23/888 |
| 2017/0218528 A1* | 8/2017 | Zhang | C25B 1/02 |

OTHER PUBLICATIONS

"High-performance asymmetric supercapacitor consisting of Ni—Co—Cu oxy-hydroxide nanosheets and activated carbon," Chien-Hung Lien et al. Electrochemistry Communications 34 (2013), pp. 323-326. (Year: 2013).*

"Synthesis and characterization of mesoporous Ni—Co oxy-hydroxides for pseudocapacitor application," Hsiang-Yu Hsu et al. Electrochimica Acta 94 (2013), pp. 104-112. (Year: 2013).*

"Ternary Ni—Co—Mo oxy-hydroxide nanoflakes grown on carbon cloth for excellent supercapacitor electrodes," Chengbing Duan et al. Materials Letters 208 (2017), pp. 65-68. (Year: 2017).*

* cited by examiner

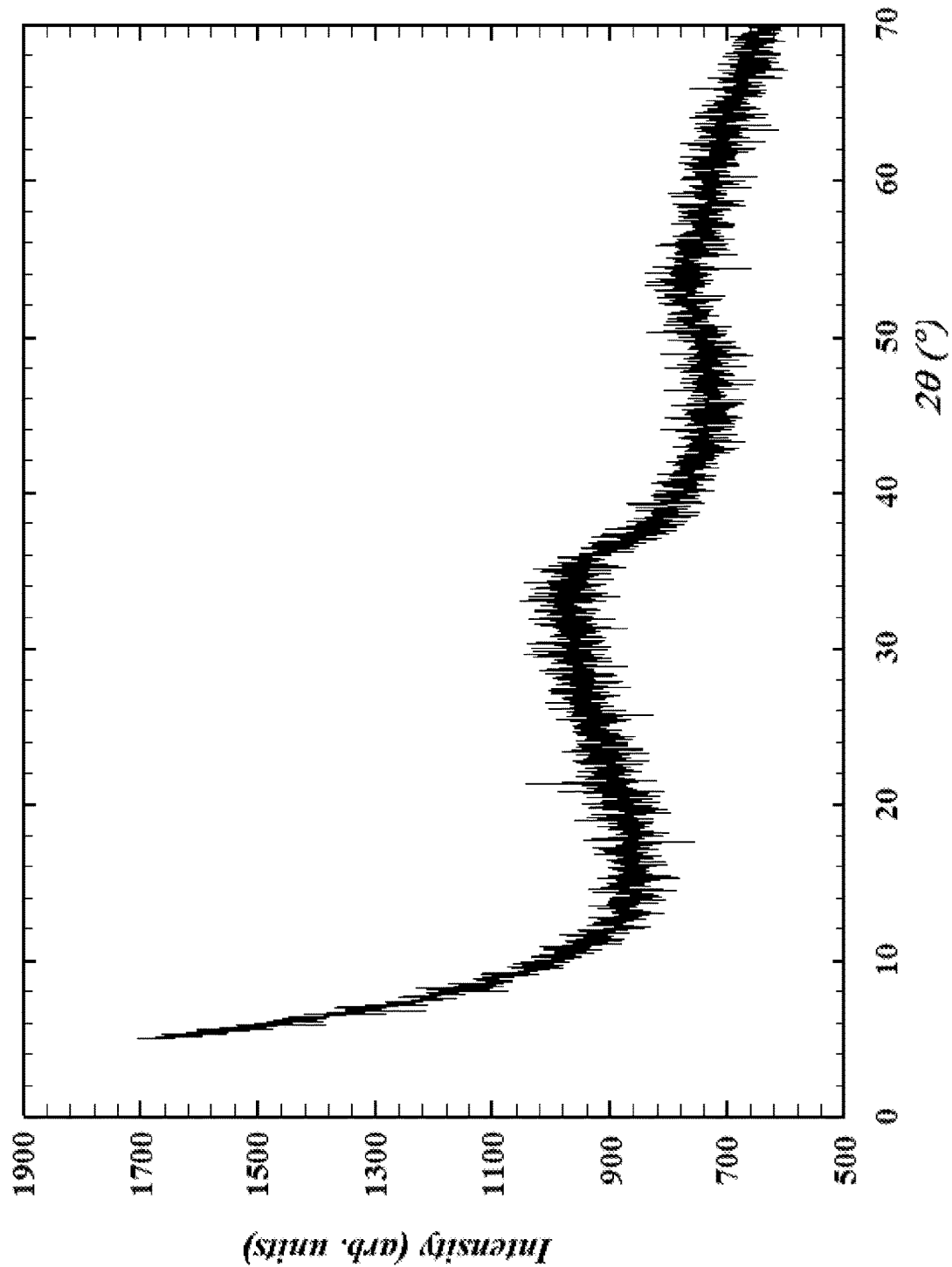

TRANSITION METAL MOLYBDOTUNGSTEN OXY-HYDROXIDE

CROSS-REFERENCE TO RELATED APPLICATIONS

This application is a Continuation of copending application Ser. No. 15/377,714 filed Dec. 13, 2016 (now U.S. Pat. No. 10,005,812), which application claims priority from Provisional Application No. 62/267,877 filed Dec. 15, 2015, the contents of which cited applications are hereby incorporated by reference in their entirety.

FIELD OF THE INVENTION

This invention relates to a new hydroprocessing catalyst. More particularly this invention relates to a transition metal molybdotungsten oxy-hydroxide material and its use as a hydroprocessing catalyst, including hydrodenitrification, hydrodesulfurization, hydrodemetallation, hydrodesilication, hydrodearomatization, hydroisomerization, hydrotreating, hydrofining, and hydrocracking.

BACKGROUND

In order to meet the growing demand for petroleum products there is greater utilization of sour crudes, which when combined with tighter environmental legislation regarding the concentration of nitrogen and sulfur within fuel, leads to accentuated refining problems. The removal of sulfur (hydrodesulfurization—HDS) and nitrogen (hydrodenitrification—HDN) containing compounds from fuel feed stocks is targeted during the hydrotreating steps of refining and is achieved by the conversion of organic nitrogen and sulfur to ammonia and hydrogen sulfide respectively.

Since the late 1940s the use of catalysts containing nickel (Ni) and molybdenum (Mo) or tungsten (W) have demonstrated up to 80% sulfur removal. See for example, V. N. Ipatieff, G. S. Monroe, R. E. Schaad, Division of Petroleum Chemistry, 115$^{th}$ Meeting ACS, San Francisco, 1949. For several decades now there has been an intense interest directed towards the development of materials to catalyze the deep desulfurization, in order to reduce the sulfur concentration to the ppm level. Some recent breakthroughs have focused on the development and application of more active and stable catalysts targeting the production of feeds for ultra low sulfur fuels. Several studies have demonstrated improved HDS and HDN activities through elimination of the support such as, for example, $Al_2O_3$. Using bulk unsupported materials provides a route to increase the active phase loading in the reactor as well as providing alternative chemistry to target these catalysts.

More recent research in this area has focused on the ultra deep desulfurization properties achieved by a Ni—Mo/W unsupported 'trimetallic' material reported in, for example, U.S. Pat. No. 6,156,695. The controlled synthesis of a broadly amorphous mixed metal oxide consisting of molybdenum, tungsten and nickel, significantly outperformed conventional hydrotreating catalysts. The structural chemistry of the tri-metallic mixed metal oxide material was likened to the hydrotalcite family of materials, referring to literature articles detailing the synthesis and characterization of a layered nickel molybdate material, stating that the partial substitution of molybdenum with tungsten leads to the production of a broadly amorphous phase which, upon decomposition by sulfidation, gives rise to superior hydrotreating activities.

The chemistry of these layered hydrotalcite-like materials was first reported by H. Pezerat, contribution à l'étude des molybdates hydrates de zinc, cobalt et nickel, C. R. Acad. Sci., 261, 5490, who identified a series of phases having ideal formulas $MMoO_4.H_2O$, $AHM_2O^-$ $(MoO_4)_2.H_2O$, and $A_{2-x}(H_3O)_xM_2O(MoO_4)_2$ where A can be $NH_4^+$, $Na^+$ or $K^+$ and M can be $Zn^{2+}$, $Co^{2+}$ or $Ni^{2+}$.

Pezerat assigned the different phases he observed as being Φc, Φy or Φy and determined the crystal structures for Φx and Φy, however owing to a combination of the small crystallite size, limited crystallographic capabilities and complex nature of the material, there were doubts raised as to the quality of the structural assessment of the materials. During the mid 1970s, Clearfield et al attempted a more detailed analysis of the Φx and Φy phases, see examples A. Clearfield, M. J. Sims, R. Gopal, Inorg. Chem., 15, 335; A. Clearfield, R. Gopal, C. H. Saldarriaga-Molina, Inorg. Chem., 16, 628. Single crystal studies on the product from a hydrothermal approach allowed confirmation of the Φx structure, however they failed in their attempts to synthesize Φy and instead synthesized an alternative phase, Na—Cu(OH)(MoO_4), see A. Clearfield, A. Moini, P. R. Rudolf, Inorg. Chem., 24, 4606.

The structure of Φy was not confirmed until 1996 when by Ying et al. Their investigation into a room temperature chimie douce synthesis technique in the pursuit of a layered ammonium zinc molybdate led to a metastable aluminum-substituted zincite phase, prepared by the calcination of Zn/Al layered double hydroxide $(Zn_4Al_2(OH)_{12}CO_3.zH_2O)$. See example D. Levin, S. L. Soled, J. Y. Ying, Inorg. Chem., 1996, 35, 4191-4197. This material was reacted with a solution of ammonium heptamolybdate at room temperature to produce a highly crystalline compound, the structure of which could not be determined through conventional ab-initio methods. The material was indexed, yielding crystallographic parameters which were the same as that of an ammonium nickel molybdate, reported by Astier, see example M. P. Astier, G. Dji, S. Teichner, J. Ann. Chim. (Paris), 1987, 12, 337, a material belonging to a family of ammonium-amine-nickel-molybdenum oxides closely related to Pezerat's materials. Astier did not publish any detailed structural data on this family of materials, leading to Ying et al reproducing the material to be analyzed by high resolution powder diffraction in order to elucidate the structure. Ying et al named this class of materials 'layered transition-metal molybdates' or LTMs.

SUMMARY OF THE INVENTION

In accordance with this invention, a unique transition metal molybdotungsten oxy-hydroxide composition is produced and can be decomposed, and optionally sulfided, to yield an active hydroprocessing catalyst. The transition metal molybdotungsten oxy-hydroxide material has a poorly crystalline x-ray powder diffraction pattern showing a broad peak between d-spacing 4.45 and 2.25 Å.

The transition metal molybdotungsten oxy-hydroxide material has the formula:

where 'S' is selected from glucose, fructose, galactose lactose, maltose, sucrose, and mixtures thereof; 'a' varies between 0.001 to 5, or between 0.1 and 3, or from 0.5 to 2; 'b' varies between 0.1 and 3; 'M' is a metal selected from Mg, Mn, Fe, Co Ni, Cu, Zn and mixtures thereof; 'c' varies from 0.1 to 2; 'x' varies from 0.01 to 1, or from 0.1 to 0.75, or from 0.2 to 0.5; 'y' varies from 0.1 to 4, or from 0.5 to 2, or from 0.8 to 1.25; the sum of (x+y) must be ≤4.01 or ≤2; z is a number which satisfies the sum of the valences of M, b, c, x and y; the material having a poorly crystalline x-ray powder diffraction pattern showing a broad peak between d-spacing 4.45 and 2.25 Å.

Another embodiment involves a method of making a unique transition metal molybdotungsten oxy-hydroxide material having the formula:

$$S_a(NH_4)_bM(OH)_cMo_xW_yO_z$$

where 'S' is selected from glucose, fructose, galactose lactose, maltose, sucrose, and mixtures thereof; 'a' varies between 0.001 to 5, or between 0.1 and 3, or from 0.5 to 2; 'b' varies between 0.1 and 3; 'M' is a metal selected from Mg, Mn, Fe, Co Ni, Cu, Zn and mixtures thereof; 'c' varies from 0.1 to 2; 'x' varies from 0.01 to 1, or from 0.1 to 0.75, or from 0.2 to 0.5; 'y' varies from 0.1 to 4, or from 0.5 to 2, or from 0.8 to 1.25; the sum of (x+y) must be ≤4.01 or ≤2; z is a number which satisfies the sum of the valences of M, b, c, x and y; the material having a poorly crystalline x-ray powder diffraction pattern showing a broad peak between d-spacing 4.45 and 2.25 Å, the method comprising forming a reaction mixture containing $NH_3$, $H_2O$, and sources of S, M, Mo, and W; adjusting the pH of the reaction mixture to a pH of from about 8.5 to about 10; reacting the reaction mixture; and recovering the metal molybdotungsten oxy-hydroxide material.

Yet another embodiment involves a conversion process comprising contacting a feed with a catalyst at conversion conditions to provide at least one product, the catalyst comprising a component produced upon decomposition by sulfidation of a transition metal molybdotungsten oxy-hydroxide material having the formula:

$$S_a(NH_4)_bM(OH)_cMo_xW_yO_z$$

where 'S' is selected from glucose, fructose, galactose lactose, maltose, sucrose, and mixtures thereof; 'a' varies between 0.001 to 5, or between 0.1 and 3 or from 0.5 to 2; 'b' varies between 0.1 and 3; 'M' is a metal selected from Mg, Mn, Fe, Co Ni, Cu, Zn and mixtures thereof; 'c' varies from 0.1 to 2; 'x' varies from 0.01 to 1, or from 0.1 to 0.75, or from 0.2 to 0.5; 'y' varies from 0.1 to 4, or from 0.5 to 2 and most or from 0.8 to 1.25; the sum of (x+y) must be ≤4.01 or ≤2; z is a number which satisfies the sum of the valences of M, b, c, x and y; the material having a poorly crystalline x-ray powder diffraction pattern showing a broad peak between d-spacing 4.45 and 2.25 Å.

Additional features and advantages of the invention will be apparent from the description of the invention, drawing and claims provided herein.

BRIEF DESCRIPTION OF THE DRAWING

The FIG. 1s the x-ray powder diffraction pattern of unique transition metal molybdotungsten oxy-hydroxide, as represented by Examples 1-3.

DETAILED DESCRIPTION OF THE INVENTION

The present invention relates to a unique transition metal molybdotungsten oxy-hydroxide, a process for preparing the composition, and a conversion process using the composition as the catalyst. The material has the designation UPM-15. This composition has an empirical formula:

$$S_a(NH_4)_bM(OH)_cMo_xW_yO_z$$

where 'S' is selected from glucose, fructose, galactose lactose, maltose, sucrose, and mixtures thereof; 'a' varies between 0.001 to 5, or between 0.1 and 3, or from 0.5 to 2; 'b' varies between 0.1 and 3; 'M' is a metal selected from Mg, Mn, Fe, Co Ni, Cu, Zn and mixtures thereof; 'c' varies from 0.1 to 2; 'x' varies from 0.01 to 1, or from 0.1 to 0.75, or from 0.2 to 0.5; 'y' varies from 0.1 to 4, or from 0.5 to 2, or from 0.8 to 1.25; the sum of (x+y) must be ≤4.01 or ≤2; z is a number which satisfies the sum of the valences of M, b, c, x and y; the material having a poorly crystalline x-ray powder diffraction pattern showing a broad peak between d-spacing 4.45 and 2.25 Å.

The composition of the invention is characterized by having an extended network of M-O-M and M-(OH)-M linkages, where M represents a metal, or combination of metals listed above. The structural units repeat itself into at least two adjacent unit cells without termination of the bonding. The composition can have a one-dimensional network, such as for example, linear chains.

The unique transition metal molybdotungsten oxy-hydroxide having its x-ray powder diffraction pattern showing a lack of crystallinity, characterized by a broad peak between d-spacing 4.45 and 2.25 Å.

The transition metal molybdotungsten oxy-hydroxide of the invention having the x-ray powder diffraction pattern shown in the FIGURE.

The transition metal molybdotungsten oxy-hydroxide composition is prepared by solvothermal crystallization of a reaction mixture typically prepared by mixing reactive sources of molybdenum and tungsten with the appropriate metal 'M' with a solvent as well as a source of ammonia and mono or disaccharide (cyclic or acylic). Specific examples of the molybdenum source which may be utilized in this invention include but are not limited to molybdenum trioxide, ammonium dimolybdate, ammonium thiomolybdate, and ammonium heptamolybdate. Specific examples of the tungsten source which may be utilized in this invention include but are not limited to tungstun trioxide, ammonium ditungstate, ammonium thiotungstate, ammonium heptatungstate, ammonium paratungstate and ammonium metatungstate. Sources of other metals, "M" include but are not limited to the respective halide, acetate, nitrate, carbonate, thiols and hydroxide salts. Specific examples include nickel chloride, cobalt chloride, nickel bromide, cobalt bromide, magnesium chloride, nickel nitrate, cobalt nitrate, iron nitrate, manganese nitrate, zinc nitrate, nickel acetate, cobalt acetate, iron acetate, nickel carbonate, cobalt carbonate, zinc carbonate, nickel hydroxide and cobalt hydroxide.

The source of ammonia may include but is not limited to ammonium hydroxide, ammonium carbonate, ammonium bicarbonate, ammonium chloride, ammonium fluoride or a combination thereof.

The source of "S" is a saccharide (mono or di) and may include, but is not limited to glucose, fructose, galactose lactose, maltose or sucrose or a combination thereof.

Generally, the process used to prepare the composition of this invention involves forming a reaction mixture wherein all of the components, such as for example, S, M, Mo, W, and $H_2O$ are mixed in solution together. By way of one specific example, a reaction mixture may be formed which in terms of molar ratios of the oxides is expressed by the formula:

$$S:AMO_x:BMoO_y:CWO_z:DNH_3:H_2O$$

where 'S' can be glucose, fructose, galactose, lactose, maltose, sucrose and mixtures thereof; the molar ratio of 'S' can vary from 0.001 to 2, or between 0.01 to 1, or from 0.1 to 1; 'M' is selected from the group consisting of iron, cobalt, nickel, manganese, copper, zinc and mixtures thereof; 'A', represents the molar ratio of M and varies from 0.1 to 2, or from 0.5 to 1.5, or from 0.75 to 1; 'x' satisfies the valency of M; 'B' represents the molar ratio of Mo and varies from 0.01 to 2, or from 0.1 to 1.5, or from 0.25 to 1; 'y' is a number which satisfies the valency of Mo 'C' represents the molar ratio of W and varies from 0.1 to 3, or from 0.5 to 2, or from 0.75 to 1.25; 'y' is a number which satisfies the valency of W; 'B' is the molar ratio of $NH_3$ and varies from 0.01 to 100, or from 1 to 50, or from 5 to 20; the molar ratio of $H_2O$ may vary from 1 to 900, or from 10 to 600, or from 50 to 300.

It is necessary to adjust the pH of the mixture to a value of about 10. The pH of the mixture can be controlled through the addition of a base such as $NH_4OH$, quaternary ammonium hydroxides, amines, and the like.

Once the reaction mixture is formed, the reaction mixture is reacted at temperatures ranging from about 60° C. to about 250° C. for a period of time ranging from 30 minutes to around 2 days. In one embodiment the temperature range for the reaction is from about 70° C. to about 180° C. and in another embodiment the temperature range of from about 80° C. to about 140° C. In one embodiment, the reaction time is from about 1 hour to about 48 hours, and in another embodiment the reaction time is from about 2 hours to about 12 hours. The reaction is carried out under atmospheric pressure or in a sealed vessel under autogenous pressure. In one embodiment the synthesis may be conducted in an open vessel under reflux conditions. The transition metal molybdotungsten oxy-hydroxide is characterized by the x-ray powder diffraction pattern shown in the FIGURE.

Once formed, the transition metal molybdotungsten oxy-hydroxide may have a binder incorporated, where the selection of binder includes but is not limited to, anionic and cationic clays such as hydrotalcites, pyroaurite-sjogrenite-hydrotalcites, montmorillonite and related clays, kaolin, sepiolites, silicas, alumina such as (pseudo) boehomite, gibbsite, flash calcined gibbsite, eta-alumina, zicronica, titania, alumina coated titania, silica-alumina, silica coated alumina, alumina coated silicas and mixtures thereof, or other materials generally known as particle binders in order to maintain particle integrity. These binders may be applied with or without peptization. The binder may be added to the bulk crystalline ammonia metal molybdate composition, and the amount of binder may range from about 1 to about 30 wt % of the finished catalysts, or from about 5 to about 26 wt % of the finished catalyst. The binder may be chemically bound to the transition metal molybdotungsten oxy-hydroxide, or may be present in a physical mixture with the transition metal molybdotungsten oxy-hydroxide.

The transition metal molybdotungsten oxy-hydroxide, with or without an incorporated binder can then be sulfided or pre-sulfided under a variety of sulfidation conditions, these include through contact of the transition metal molybdotungsten oxy-hydroxide with a sulfur containing feed as well as the use of a gaseous mixture of $H_2S/H_2$. The sulfidation of transition metal molybdotungsten oxy-hydroxide is performed at elevated temperatures, typically ranging from 50 to 600° C., or from 150 to 500° C., or from 250 to 450° C.

The unsupported transition metal molybdotungsten oxy-hydroxide material of this invention can be used as a catalyst or catalyst support in various hydrocarbon conversion processes. Hydroprocessing is one class of hydrocarbon conversion processes in which the crystalline ammonia metal molybdate material is useful as a catalyst. Examples of specific hydroprocessing processes are well known in the art and include hydrodenitrification, hydrodesulfurization, hydrodemetallation, hydrodesilication, hydrodearomatization, hydroisomerization, hydrotreating, hydrofining, and hydrocracking.

The operating conditions of the hydroprocessing processes listed above typically include reaction pressures from about 2.5 MPa to about 17.2 MPa, or in the range of about 5.5 to about 17.2 MPa, with reaction temperatures in the range of about 245° C. to about 440° C., or in the range of about 285° C. to about 425° C. Time with which the feed is in contact with the active catalyst, referred to as liquid hour space velocities (LHSV), should be in the range of about 0.1 $h^{-1}$ to about 10 $h^{-1}$, or about 2.0 $h^{-1}$ to about 8.0 $h^{-1}$. Specific subsets of these ranges may be employed depending upon the feedstock being used. For example when hydrotreating a typical diesel feedstock, operating conditions may include from about 3.5 MPa to about 8.6 MPa, from about 315° C. to about 410° C., from about 0.25/h to about 5/h, and from about 84 $Nm^3H_2/m^3$ to about 850 $Nm^3H_2/m^3$ feed. Other feedstocks may include gasoline, naphtha, kerosene, gas oils, distillates, and reformate.

Examples are provided below so that the invention may be described more completely. These examples are only by way of illustration and should not be interpreted as a limitation of the broad scope of the invention, which is set forth in the appended claims.

X-ray powder diffraction patterns presented in the following examples were obtained using standard x-ray powder diffraction techniques. The radiation source was a high-intensity, x-ray tube operated at 45 kV and 35 mA. The diffraction pattern from the copper K-alpha radiation was obtained by appropriate computer based techniques. Powder samples were pressed flat into a plate and continuously scanned from 3° and 70° (2θ). Interplanar spacings (d) in Angstrom units were obtained from the position of the diffraction peaks expressed as θ, where θ is the Bragg angle as observed from digitized data. As will be understood by those skilled in the art the determination of the parameter 2θ is subject to both human and mechanical error, which in combination can impose an uncertainty of about ±0.4° on each reported value of 2θ. This uncertainty is also translated to the reported values of the d-spacings, which are calculated from the 2θ values.

In certain instances the purity of a synthesized product may be assessed with reference to its x-ray powder diffraction pattern. Thus, for example, if a sample is stated to be pure, it is intended only that the x-ray pattern of the sample is free of lines attributable to crystalline impurities. As will be understood to those skilled in the art, it is possible for different poorly crystalline materials to yield a peak at the same position. If a material is composed of multiple poorly crystalline materials, then the peak positions observed individually for each poorly crystalline materials would be observed in the resulting summed diffraction pattern. Likewise it is possible to have some peaks appear at the same positions within different, single phase, crystalline materials, which may be simply a reflection of a similar distance within the materials and not that the materials possess the same structure.

Example 1

In a 1 liter flask, 8.97 g of ammonium heptamolybdate (0.05 moles of Mo) and 12.68 g of ammonium metatungstate (0.05 moles of W) were dissolved in 160 g of deionized $H_2O$ and 40 ml of concentrated ammonium hydroxide. To this solution, 18.01 g of glucose (0.1 mole) was added to yield a clear solution, Solution A. Solution B was prepared where 29.08 g of nickel nitrate hexahydrate (0.1 moles of Ni) was completely dissolved in 50 g of deionized H$_2$O. Solution B was added to solution A over a period of 10 minutes, resulting in the formation of a light blue slurry which was then refluxed at about 100° C. for 4 hours, forming a green precipitate. This precipitate was cooled to room temperature, filtered, washed with 90 ml of about 90° C. water and then dried at 100° C. X-ray diffraction of the dried precipitate matches the spectra shown in the FIGURE.

Example 2

In a 1 liter flask, 5.38 g of ammonium heptamolybdate (0.03 moles of Mo) and 17.75 g of ammonium metatungstate (0.07 moles of W) were dissolved in 160 g of deionized H$_2$O and 40 ml of concentrated ammonium hydroxide. To this solution, 18.01 g of glucose (0.1 mole) was added to yield a clear solution, Solution A. Solution B was prepared where 29.08 g of nickel nitrate hexahydrate (0.1 moles of Ni) was completely dissolved in 50 g of deionized H$_2$O. Solution B was added to solution A over a period of 10 minutes, resulting in the formation of a light blue slurry which was then refluxed at about 100° C. for 4 hours, forming a green precipitate. This precipitate was cooled to room temperature, filtered, washed with 90 ml of about 90° C. water and then dried at 100° C. X-ray diffraction of the dried precipitate matches the spectra shown in the FIGURE.

Example 3

In a 1 liter flask, 5.38 g of ammonium heptamolybdate (0.3 moles of Mo) and 20.32 g of ammonium metatungstate (0.08 moles of W) were dissolved in 160 g of deionized H$_2$O and 40 ml of concentrated ammonium hydroxide. To this solution, 4.5 g of glucose (0.025 mole) was added to yield a clear solution, Solution A. Solution B was prepared where 23.7 g of cobalt chloride (0.1 moles of Co) was completely dissolved in 50 g of deionized H$_2$O. Solution B was added to solution A over a period of 10 minutes, resulting in the formation of a light blue slurry which was then refluxed at about 100° C. for 4 hours, forming a precipitate. This precipitate was cooled to room temperature, filtered, washed with 90 ml of about 90° C. water and then dried at 100° C. X-ray diffraction of the dried precipitate matches the spectra shown in the FIGURE.

EMBODIMENTS

Embodiment 1 is a unique transition metal molybdotungsten oxy-hydroxide material having the formula:

where 'S' is selected from glucose, fructose, galactose lactose, maltose, sucrose, and mixtures thereof; 'a' varies between 0.001 to 5, or between 0.1 and 3, or from 0.5 to 2; 'b' varies between 0.1 and 3; 'M' is a metal selected from Mg, Mn, Fe, Co Ni, Cu, Zn and mixtures thereof; 'c' varies from 0.1 to 2; 'x' varies from 0.01 to 1, or from 0.1 to 0.75, or from 0.2 to 0.5; 'y' varies from 0.1 to 4, or from 0.5 to 2, or from 0.8 to 1.25; the sum of (x+y) must be ≤4.01 or ≤2; z is a number which satisfies the sum of the valences of M, b, c, x and y; the material having a poorly crystalline x-ray powder diffraction pattern showing a broad peak between d-spacing 4.45 and 2.25 Å.

The transition metal molybdotungsten oxy-hydroxide material of embodiment 1 wherein the transition metal molybdotungsten oxy-hydroxide material is present in a mixture with at least one binder and wherein the mixture comprises up to 25 wt % binder.

The transition metal molybdotungsten oxy-hydroxide material of embodiment 1 wherein the transition metal molybdotungsten oxy-hydroxide material is present in a mixture with at least one binder, wherein the mixture comprises up to 25 wt % binder, and wherein the binder is selected from the group consisting of silicas, aluminas, and silica-aluminas.

The transition metal molybdotungsten oxy-hydroxide material of embodiment 1 wherein M is nickel or cobalt.

The transition metal molybdotungsten oxy-hydroxide material of embodiment 1 wherein M is nickel.

The transition metal molybdotungsten oxy-hydroxide material of embodiment 1 wherein the transition metal molybdotungsten oxy-hydroxide material is sulfided.

Embodiment 2 is a method of making a transition metal molybdotungsten oxy-hydroxide material having the formula:

where 'S' is selected from glucose, fructose, galactose lactose, maltose, sucrose, and mixtures thereof; 'a' varies between 0.001 to 5, or between 0.1 and 3, or from 0.5 to 2; 'b' varies between 0.1 and 3; 'M' is a metal selected from Mg, Mn, Fe, Co Ni, Cu, Zn and mixtures thereof; 'c' varies from 0.1 to 2; 'x' varies from 0.01 to 1, or from 0.1 to 0.75, or from 0.2 to 0.5; 'y' varies from 0.1 to 4, or from 0.5 to 2, or from 0.8 to 1.25; the sum of (x+y) must be ≤4.01 or ≤2; z is a number which satisfies the sum of the valences of M, b, c, x and y; the material having a poorly crystalline x-ray powder diffraction pattern showing a broad peak between d-spacing 4.45 and 2.25 Å, the method comprising: (a) forming a reaction mixture containing NH$_3$, H$_2$O, and sources of S, M, Mo, and W; (b) adjusting the pH of the reaction mixture to a pH of from about 8.5 to about 10; (c) reacting the reaction mixture; (d) recovering the transition metal molybdotungsten oxy-hydroxide material.

The method of embodiment 2 wherein the reacting is conducted at a temperature ranging from about 60° C. to about 120° C. for a period of time ranging from 30 minutes to around 2 days.

The method of embodiment 2 wherein the recovering is by filtration or centrifugation.

The method of embodiment 2 further comprising adding a binder to the recovered metal molybdotungsten oxy-hydroxide material.

The method of embodiment 2 further comprising adding a binder to the recovered metal molybdotungsten oxy-hydroxide material and wherein the binder is selected from the group consisting of aluminas, silicas, and alumina-silicas.

The method of embodiment 2 further comprising sulfiding the recovered transition metal molybdotungsten oxy-hydroxide material.

Embodiment 3 is a conversion process comprising contacting a feed with a catalyst at conversion conditions to provide at least one product, the catalyst comprising a component produced upon decomposition by sulfidation of a transition metal molybdotungsten oxy-hydroxide material having the formula:

where 'S' is selected from glucose, fructose, galactose lactose, maltose, sucrose, and mixtures thereof; 'a' varies between 0.001 to 5, or between 0.1 and 3, or from 0.5 to 2; 'b' varies between 0.1 and 3; 'M' is a metal selected from Mg, Mn, Fe, Co Ni, Cu, Zn and mixtures thereof; 'c' varies from 0.1 to 2; 'x' varies from 0.01 to 1, or from 0.1 to 0.75, or from 0.2 to 0.5; 'y' varies from 0.1 to 4, or from 0.5 to 2, or from 0.8 to 1.25; the sum of (x+y) must be ≤4.01 or ≤2; z is a number which satisfies the sum of the valences of M, b, c, x and y; the material having a poorly crystalline x-ray powder diffraction pattern showing a broad peak between d-spacing 4.45 and 2.25 Å.

The process of embodiment 3 wherein the conversion process is hydroprocessing.

The process of embodiment 3 wherein the conversion process is selected from the group consisting of hydrodenitrification, hydrodesulfurization, hydrodemetallation, hydrodesilication, hydrodearomatization, hydroisomerization, hydrotreating, hydrofining, and hydrocracking.

The process of embodiment 3 wherein the catalyst is present in a mixture with at least one binder and wherein the mixture comprises up to 25 wt % binder. The process of embodiment 3 wherein the binder is selected from the group consisting of silicas, aluminas, and silica-aluminas.

The invention claimed is:

1. A conversion process comprising contacting a feed with a catalyst at conversion conditions to provide at least one product, the catalyst comprising a component produced upon decomposition by sulfidation of a transition metal molybdotungsten oxy-hydroxide material having the formula:

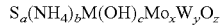

$$S_a(NH_4)_b M(OH)_c Mo_x W_y O_z$$

where 'S' is selected from glucose, fructose, galactose, lactose, maltose, sucrose, and mixtures thereof; 'a' varies between 0.001 to 5; 'b' varies between 0.1 and 3; 'M' is a metal selected from Mg, Mn, Fe, Co Ni, Cu, Zn and mixtures thereof; 'c' varies from 0.1 to 2; 'x' varies from 0.01 to 1; 'y' varies from 0.1 to 4; the sum of (x+y) must be ≤4.0; z is a number which satisfies the sum of the valences of M, b, c, x and y; the material having a poorly crystalline x-ray powder diffraction pattern showing a broad peak between d-spacing 4.45 and 2.25 Å.

2. The process of claim 1 wherein the conversion process is hydrodenitrification, hydrodesulfurization, hydrodemetallation, hydrodesilication, hydrodearomatization, hydroisomerization, hydrotreating, hydrofining, or hydrocracking.

3. The process of claim 1 wherein the conversion process is hydroprocessing.

4. The process of claim 1 wherein the catalyst is present in a mixture with at least one binder and wherein the mixture comprises up to 25 wt % binder.

5. The process of claim 1 wherein the binder is selected from the group consisting of silicas, aluminas, and silica-aluminas.

6. The process of claim 1 wherein M of the transition metal molybdotungsten oxy-hydroxide material is nickel or cobalt.

7. The process of claim 1 wherein M of the transition metal molybdotungsten oxy-hydroxide material is nickel.

8. The process of claim 1 wherein the feed comprises sulfur and the sulfidation comprises contacting the transition metal molybdotungsten oxy-hydroxide material with the sulfur containing feed.

9. The process of claim 1 wherein the sulfidation comprises contacting the transition metal molybdotungsten oxyhydroxide material with a gaseous mixture of $H_2S/H_2$.

10. The process of claim 1 wherein the sulfidation is conducted at a temperature ranging from about 50° C. to about 600° C.

11. The process of claim 1 wherein the sulfidation is conducted at a temperature ranging from about 150° C. to about 500° C.

12. The process of claim 1 wherein the sulfidation is conducted at a temperature ranging from about 250° C. to about 450° C.

* * * * *